(12) United States Patent
Wright et al.

(10) Patent No.: US 6,346,380 B1
(45) Date of Patent: *Feb. 12, 2002

(54) DETECTION OF VARIATIONS IN HUMAN H2 RECEPTORS

(75) Inventors: Simon Wright; Paul Heath, both of Sheffield; Paul Orange, Stockport; Ronald Carl Alan Pearson, Newcastle, all of (GB)

(73) Assignee: Unisheff Ventures Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/171,456

(22) PCT Filed: Apr. 18, 1997

(86) PCT No.: PCT/GB97/01075

§ 371 Date: Aug. 3, 1999

§ 102(e) Date: Aug. 3, 1999

(87) PCT Pub. No.: WO97/40186

PCT Pub. Date: Oct. 30, 1997

(30) Foreign Application Priority Data

Apr. 19, 1996 (GB) .............................................. 9608168

(51) Int. Cl.[7] .......................... C12Q 1/68; C07H 21/04; C12P 19/34; C12N 9/16

(52) U.S. Cl. ....................... 435/6; 536/24.33; 536/24.3; 536/24.31; 536/23.5; 536/24.5; 435/91.1; 435/91.2; 435/196

(58) Field of Search ................................ 536/23.1, 24.5, 536/24.33, 23.5, 24.3, 126; 435/6, 69.1, 91.2, 320.1, 91.1, 325, 810, 24.31, 196

(56) References Cited

U.S. PATENT DOCUMENTS 5,885,824 A * 3/1999 Yamada .................... 435/252.3
6,015,888 A * 1/2000 Heath et al. ............... 536/23.5

OTHER PUBLICATIONS

Ahern, H. Biochemical, Reagent Kits Offer Scientist Good Return on Investment. The Scientist. vol. 9, No. 15, pp. 1–5, Jul. 24, 1995.*
Gantz et al. Molecular cloning of the human histamine H2 receptor. biochemical and Biophysical research communications, vol. 178, No. 3, pp. 1386–1392, 1991.*

* cited by examiner

Primary Examiner—Stephanie W. Zitomer
Assistant Examiner—Cynthia Wilder
(74) Attorney, Agent, or Firm—Fish & Richardson, P.C.

(57) ABSTRACT

A group of oligonucleotides for the identification of sequences in a sample comprising human histamine $H_2$ receptor DNA, cDNA or RNA originating from a tissue sample or body fluid is employed in the diagnosis and/or treatment of human neurological and psychiatric disorders, particularly schizophrenia, and diseases of other systems or organs of the human body. The oligonucleotides, suitable for use as primers for the amplification of DNA corresponding to a region of a human histamine $H_2$ receptor, have nucleotide sequences selected from: 5'ACACCAGCCTGGAT-GTGA 3'(as listed in SEQ ID NO:12), 5'TCACATCCAG-GCTGGTCT 3' (as listed in SEQ ID NO:13), 5' CAATCATACCACCTCTAA 3' (as listed in SEQ ID NO:14), 5' ACACAAACGCGGTGAAGT 3'(as listed in SEQ ID NO:15). Also described is a diagnostic kit comprising one or more of the above mentioned oligonucleotides.

10 Claims, 1 Drawing Sheet

Figure 1

DETECTION OF VARIATIONS IN HUMAN H2 RECEPTORS

This is a International Patent Application No. PCT/GB97/01075, with an international filing date of Apr. 18, 1997, now pending.

TECHNICAL FIELD

This invention relates to the detection of variations in human histamine $H_2$ receptors, and more particularly to the development of new compounds useful in the sequencing and identification of a human histamine $H_2$ receptor and their use in the diagnosis and treatment of certain human disorders, for example, brain disorders. The invention also relates to new compounds and a method for detecting an allelic polymorphic variation within the human population for the gene encoding the histamine $H_2$ receptor, and their use in the diagnosis and treatment of human disorders.

BACKGROUND OF THE INVENTION

The histamine $H_2$ receptor is one of many receptors in the body. Compounds used to treat many diseases work by activating a receptor or inhibiting the action of its natural ligand. Variations in some receptors amongst the population are known to be caused by allelic variation, and this variation can alter the response of a disease to a drug amongst patients. An example of this would be the response to clozapine, used to treat schizophrenia, associated with allelic variation in the 5-$HT_{2A}$ receptor demonstrated by Arranz el al (1995) Lancet, 346(8970), 281–282.

In co-pending UK Patent Applications Nos. GB9503866.7 and GB9522889.6, and in International Patent Application No. PCT/EP96/00397, it is reported that there is a hitherto unrecognised allele or subtype of the human histamine $H_2$ receptor gene which may be specific to the brain.

In the above mentioned co-pending patent specifications there are described and claimed:

1) a sequence for a novel allele of a human histamine $H_2$ receptor gene comprising up to six single base substitutions compared with the cDNA sequence published by Gantz et al (1991) Biochem Biophys Res Comm 178,3,1386–1392 as follows:

| site of change | base change | amino acid alteration |
| --- | --- | --- |
| 398 | T-C | Val-Gly |
| 525 | A-T | Lys-Asn |
| 620 | A-G | Lys-Asp |
| 649 | A-G | Asn-Asp |
| 692 | A-G | Lys-Arg |
| 802 | G-A | Val-Met |

The cDNA sequence in Gantz et al., supra, is:

```
   1 atggcaccca atggcacagc ctcttccttt tgcctggact ctaccgcatg caagatcacc  (SEQ ID NO:18)
  61 atcaccgtgg tccttgcggt cctcatcctc atcaccgttg ctggcaatgt ggtcgtctgt
 121 ctggccgtgg gcttgaaccg ccggctccgc aacctgacca attgtttcat cgtgtccttg
 181 gctatcactg acctgctcct cggcctcctg gtgctgccct tctctgccat ctaccagctg
 241 tcctgcaagt ggagctttgg caaggtcttc tgcaatatct acaccagcct ggatgtgatg
 301 ctctgcacag cctccattct taacctcttc atgatcagcc tcgaccggta ctgcgctgtc
 361 atggaccac tgcggtaccc tgtgctggtc accccagttc gggtcgccat ctctctggtc
 421 ttaatttggg tcatctccat taccctgtcc tttctgtcta tccacctggg gtggaacagc
 481 aggaacgaga ccagcaaggg caatcatacc acctctaagt gcaaagtcca ggtcaatgaa
 541 gtgtacgggc tggtggatgg gctggtcacc ttctacctcc cgctactgat catgtgcatc
 601 acctactacc gcatcttcaa ggtcgcccgg gatcaggcca agaggatcaa tcacattagc
 661 tcctggaagg cagccaccat cagggagcac aaagccacag tgacactggc cgccgtcatg
 721 ggggccttca tcatctgctg gtttccctac ttcaccgcgt ttgtgtaccg tgggctgaga
 781 ggggatgatg ccatcaatga ggtgttagaa gccatcgttc tgtggctggg ctatgccaac
 841 tcagccctga accccatcct gtatgctgcg ctgaacagag acttccgcac cgggtaccaa
 901 cagctcttct gctgcaggct ggccaaccgc aactcccaca aaacttctct gaggtccaac
 961 gcctctcagc tgtccaggac ccaaagccga gaacccaggc aacaggaaga gaaacccctg
1021 aagctccagg tgtggagtgg gacagaagtc acggcccccc agggagccac agacaggtaa
1081 aagctccagg tgtggagtgg gacagaagtc acggcccccc agggagccac agacaggtaa
1141 gcgctgaaca gagacttccg caccgggtac caacagctct tctgctgcag g
```

This cDNA sequence encodes the following amino acid sequence:

MAPNGTASSFCLDSTACKITITVVLAVLILITVAGNVVVCLAVGLNRRLRNLTNCFIVSLAITDLLLGLLVLPFSAI (SEQ ID NO: 19)
YQLSCKWSFGKVFCNIYTSLDVMLCTASILNLFMISLDRYCAVMDPLRYPVLVTPVRVAISLVLIWVISITLSFLSI
HLGWNSRNETSKGNHTTSKCKVQVNEVYGLVDGLVTFYLPLLIMCITYYRIFKVARDQAKRINHISSWKAATIREHK
ATVTLAAVMGAFIICWFPYFTAFVYRGLRGDDAINEVKEAIVKWLGYANSALNPILYAAKNRDFRTGYQQLFCCRLA
NRNSHKTSLRSNASQLSRTQSREPRQQEEKPLKLQVWSGTEVTAPQGATDR 2) a nucleotide sequence coding for a region of a human histamine $H_2$ receptor, comprising one or more of the following base substitutions compared with the published sequence in Gantz et al (1991) supra, and from which the positional notation is taken:

| site of change | base |
|---|---|
| 398 | C |
| 525 | T |
| 620 | G |
| 649 | G |
| 692 | G |
| 802 | A |

The nucleotide sequence can, for example, comprise the following sequence (as listed in SEQ ID NO: 1):

5'  CAGCTCGGGTCGCCATCTCTCTGGTCTTAATTTGGGTCATCTCCATTACCCTGTC

CTTTCTGTCTATCCACCTGGGGTGGAACAGCAGGAACGAGACCAGCAAGGGCAAT

CATACCACCTCTAAGTGCAATGTCCAGGTCAATGAAGTGTACGGGCTGGTGGATG

GGCTGGTCACCTTCTACCTCCCGCTACTGATCATGTGCATCACCTACTACCGCAT

CTTCAGGGTCGCCCGGGATCAGGCCAAGAGGATCGATCACATTAGCTCCTGGAAG

GCAGCCACCATCAGGGAGCACAGAGCCACAGTGACACTGGCCGCCGTCATGGGGG

CCTTCATCATCTGCTGGTTTCCCTACTTCACCGCGTTTGTGTACCGTGGGCTGAG

AGGGGATGATGCCATCAATGAGATGTTA  3'

As a specific exemplification, the nucleotide sequence can comprise the following sequence (as listed in SEQ ID NO: 2):

5'  CCAATGGCACAGCCTCTTCCTTTTGCCTGGACTCTACCGCATGCAAGATCACCAT

CACCGTGGTCCTTGCGGTCCTCATCCTCATCACCGTTGCTGGCAATGTGGTCGTC

TGTCTGGCCGTGGGCTTGAACCGCCGGCTCCGCAACCTGACCAATTGTTTCATCG

TGTCCTTGGCTATCACTGACCTGCTCCTCGGCCTCCTGGTGCTGCCCTTCTCTGC

CATCTACCAGCTGTCCTGCAAGTGGAGCTTTGGCAAGGTCTTCTGCAATATCTAC

ACCAGCCTGGATGTGATGCTCTGCACAGCCTCCATTCTTAACCTCTTCATGATCA

GCCTCGACCGGTACTGCGCTGTCATGGACCCACTGCGGTACCCTGTGCTGGTCAC

```
                                      -continued
CCCAGCTCGGGTCGCCATCTCTCTGGTCTTAATTTGGGTCATCTCCATTACCCTG

TCCTTTCTGTCTATCCACCTGGGGTGGAACAGCAGGAACGAGACCAGCAAGGGCA

ATCATACCACCTCTAAGTGCAATGTCCAGGTCAATGAAGTGTACGGGCTGGTGGA

TGGGCTGGTCACCTTCTACCTCCCGCTACTGATCATGTGCATCACCTACTACCGC

ATCTTCAGGGTCGCCCGGGATCAGGCCAAGAGGATCGATCACATTAGCTCCTGGA

AGGCAGCCACCATCAGGGAGCACAGAGCCACAGTGACACTGGCCGCCGTCATGGG

GGCCTTCATCATCTGCTGGTTTCCCTACTTCACCGCGTTTGTGTACCGTGGGCTG

AGAGGGGATGATGCCATCAATGAGATGTTAGAAGCCATCGTTCTGTGGCTGGGCT

ATGCCAACTCAGCCCTGAACCCCATCCTGTATGCTGCGCTGAACAGAGACTTCCG

CACCGGGTACCAACAGCTCTTCTGCTGCAGGCTGGCCAACCGCAACTCCCACAAA

ACTTCTCTGAGGTCCAACGCCTCTCAGCTGTCCAGGACCCAAAGCCGAGAACCCA

GGCAACAGGAAGAGAAACCCCTGAAGCTCCAGGTGTGGAGTGGGACAGAAGTCACG    3'
```

3) new oligonucleotides, suitable for use as primers for the amplification of DNA corresponding to a region of a human histamine $H_2$ receptor, having nucleotide sequences selected from:

1) 5' CCAATGGCACAGCCTCTT 3' (as listed in SEQ ID NO: 3)
2) 5' CGTGACTTCTGTCCCACT 3' (as listed in SEQ ID NO: 4)
3) 5' CCAGGCAACAGGAAGAGA 3' (as listed in SEQ ID NO: 5)
4) 5' TCTCTTCCTGTTGCCTGG 3' (as listed in SEQ ID NO: 6)
5) 5' GCAGCAGAAGAGCTGTTG 3' (as listed in SEQ ID NO: 7)
6) 5' TCCAGGTCAATGAAGTGT 3' (as listed in SEQ ID NO: 8)
7) 5' ACACTTCATTGACCTGGA 3' (as listed in SEQ ID NO: 9)
8) 5° CCAAGAGGATCAATCACA 3' (as listed in SEQ ID NO: 10)
9) 5' TGTGATTGATCCTCTTGG 3' (as listed in SEQ ID NO: 11)
and 4) a diagnostic kit comprising one or more of the above new oligonucleotides.

DISCLOSURE OF THE INVENTION

The present invention is concerned in one aspect with improvements in the diagnosis and/or treatment of human neurological and psychiatric disorders, and more particularly in the diagnosis and treatment of schizophrenia. In another aspect, the invention is concerned with improvements in the diagnosis and/or treatment of diseases of other systems or organs of the human body.

According to the invention, a further group of oligonucleotides has now been developed for the identification of sequences in a sample comprising a human histamine $H_2$ receptor DNA, cDNA or RNA originating from a tissue sample or body fluid.

In a first aspect, therefore, the invention provides new oligonucleotides, suitable for use as primers for the amplification of DNA corresponding to a region of a human histamine $H_2$ receptor, having nucleotide sequences selected from:

10) 5' ACACCAGCCTGGATGTGA 3' (as listed in SEQ ID NO:12)
11) 5' TCACATCCAGGCTGGTGT 3' (as listed in SEQ ID NO:13)
12) 5' CAATCATACCACCTCTAA 3' (as listed in SEQ ID NO:14)
13) 5' ACACAAACGCGGTGAAGT 3' (as listed in SEQ ID NO:15)
15 and a diagnostic kit comprising one or more of the above mentioned oligonucleotides.

The direction and base start numbers for the novel oligonucleotide primers are as follows:

| Primer | | Base Start No. |
|---|---|---|
| 10) | Upstream | 281 |
| 11) | Downstream | 298 |
| 12) | Upstream | 501 |
| 13) | Downstream | 766 |

Information on the human histamine $H_2$ receptor was obtained from the MRC Daresbury database accessing "Genem 61" File no. M64799—Human histamine $H_2$ receptor gene.

The above mentioned substitutions in the human histamine $H_2$ receptor gene alter and in some instances introduce or remove new sites for cleavage by specific restriction endonucleases as follows:

| base change site | alters restriction map of: |
|---|---|
| 398 | AluI, AvaI, BspWI, BsrI, CviJI |
| 525 | |
| 620 | Eco57 |
| 649 | ClaI, Sau3A, TaqI |
| 692 | |
| 802 | MnlI |

In another aspect the invention provides a diagnostic kit comprising one or more of the new oligonucleotide primers and, preferably, one or more of the above mentioned endonucleases, optionally with one or more buffers.

In a still further aspect, the invention provides a diagnostic kit comprising one or more of the new oligonucleotide primers whereby detection of human histamine subtypes can be achieved using single-stranded conformational polymorphism (SSCP). The kit can, for example, comprise one or more of the above mentioned oligonucleotide primers, and, optionally, formamide.

A kit may be used to establish genotype or base variations. This information may be used in predicting an individual's disease susceptibility, disease course, prognosis and/or response to treatment, as would be understood by those skilled in the art from the disclosure contained herein. The treatment response or efficacy which may be predicted may include drug treatment such as for example, use of $H_2$ receptor antagonists, for example, famotidine, or other forms of treatment such as social or psychological intervention.

Eucaryotic expression vectors and host cells transformed thereby can be prepared as described in the above mentioned co-pending patent specifications and the encoded protein analysed.

The invention is illustrated by the following Examples:

EXAMPLE 1

This example describes the identification and sequencing of an allelic human $H_2$ receptor gene using certain novel oligonucleotide primers according to the invention.

A polymerase chain reaction (PCR) product is prepared from human DNA.

DNA was extracted from human brain tissue by first pulverizing approximately 1g of tissue in liquid nitrogen then adding to 10 ml lysis buffer (0.32M sucrose, 10 mM Tris, 5 mM magnesium chloride 1% Triton X-100 pH8.0). This solution was centrifuged (9,000 rpm 15 mins) to pellet the tissue, the lysis buffer was drawn off and the pellet resuspended in 4.5 ml 75 mM sodium chloride, 24 mM EDTA. This solution was then incubated for 3 hours with 250 µl 10% SDS and 2 mg proteinase K at 56° C. This aqueous phase was then extracted twice with 5 ml of phenol:chloroform:isoamyl alcohol (25:24:1). Then sodium acetate to 0.3M pH7.5 and 2 volumes of ethanol (at −20° C.) were added to the aqueous phase and the DNA hooked out into TE buffer. The concentration of the DNA was determined by measuring the optical density of the sample, at a wavelength of 260 nm.

The DNA was then amplified by the polymerase chain reaction using the oligonucleotide primers 1) and 2) (as hereinbefore described) for 36 cycles. The timing for each cycle was as follows; 1 min at 94° C., 1.5 min at 56° C. and 2 mins at 72°C., this was then followed by a 10 min extension at 72° C. (Amplitaq DNA polymerase Perkin-Elmer Cetus). This reaction produced a DNA fragment of 1047 base pair when analyzed by gel electrophoresis.

Following PCR amplification of the DNA, the PCR products were immediately ligated and cloned into the TA cloning system (InvitroGen). The transformed cells were plated onto Luria-Bertani plates containing 50 µl/ml ampicillin and 1.6 mg X-Gal. Plates were then incubated overnight at 37° C., then moved to 4° C. for 4 hours to allow for colour development. Positive (white colonies) were then analyzed by growing a 5 ml culture overnight at 37° C. extracting the plasmids (Qiaspin minipreps (Qiagen)) and performing an EcoRI digest to ensure the correct size product was contained in the plasmid. The plasmid used to clone the PCR product is the PCR™ II Vector, which is transformed into One Shot™ INVαF' Competent cells.

Both strands of the cloned PCR product were sequenced using the dideoxynucleotide chain-terminated method, carried out with Sequenase version 2.0 (Amersham/USB). Partial sequencing of short stretches of the cloned DNA utilised all the oligonucleotide primers 1) to 11) hereinbefore described. The cloned PCR product was shown to be identical to the gastric cDNA of Gantz et, al except for the previously mentioned six single base changes.

Results and Discussions

The sequence derived from the above described method is listed below and in SEQ ID NO: 2. The novel form of the human Histamine $H_2$ receptor gene is designated the $H_2R_{549G}$ allele (SEQ ID NO:2), and the original form as described by Gantz et al is designated the $H_2R_{649A}$ allele, as described by Orange et al (1996) Neuro Report 7(7) (to be published).

```
5'  AATGGCACAGCCTCTTCCTTTTGCCTGGACTCTACCGCATGCAAGATCACCAT

CACCGTGGTCCTTGCGGTCCTCATCCTCATCACCGTTGCTGGCAATGTGGTCGTC

TGTCTGGCCGTGGGCTTGAACCGCCGGCTCCGCAACCTGACCAATTGTTTCATCG

TGTCCTTGGCTATCACTGACCTGCTCCTCGGCCTCCTGGTGCTGCCCTTCTCTGC

CATCTACCAGCTGTCCTGCAAGTGGAGCTTTGGCAAGGTCTTCTGCAATATCTAC

ACCAGCCTGGATGTGATGCTCTGCACAGCCTCCATTCTTAACCTCTTCATGATCA

GCCTCGACCGGTACTGCGCTGTCATGGACCCACTGCGGTACCCTGTGCTGGTCAC

CCCAGCTCGGGTCGCCATCTCTCTGGTCTTAATTTGGGTCATCTCCATTACCCTG

TCCTTTCTGTCTATCCACCTGGGGTGGAACAGCAGGAACGAGACCAGCAAGGGCA

ATCATACCACCTCTAAGTGCAATGTCCAGGTCAATGAAGTGTACGGGCTGGTGGA

TGGGCTGGTCACCTTCTACCTCCCGCTACTGATCATGTGCATCACCTACTACCGC

ATCTTCAGGGTCGCCCGGGATCAGGCCAAGAGGATCGATCACATTAGCTCCTGGA

AGGCAGCCACCATCAGGGAGCACAGAGCCACAGTGACACTGGCCGCCGTCATGGG

GGCCTTCATCATCTGCTGGTTTCCCTACTTCACCGCGTTTGTGTACCGTGGGCTG
```

-continued

```
AGAGGGGATGATGCCATCAATGAGATGTTAGAAGCCATCGTTCTGTGGCTGGGCT

ATGCCAACTCAGCCCTGAACCCCATCCTGTATGCTGCGCTGAACAGAGACTTCCG

CACCGGGTACCAACAGCTCTTCTGCTGCAGGCTGGCCAACCGCAACTCCCACAAA

ACTTCTCTGAGGTCCAACGCCTCTCAGCTGTCCAGGACCCAAAGCCGAGAACCCA

GGCAACAGGAAGAGAAACCCCTGAAGCTCCAGGTGTGGAGTGGGACAGAAGTCACG   3'
```

EXAMPLE 2

This example describes the identification and sequencing of an allelic human $H_2$ receptor gene using certain novel oligonucleotide primers according to the invention.

The example describes confirmation of the existence of polymorphisms in the human histamine $H_2$ receptor gene utilising single-stranded conformational polymorphism (SSCP). This is made possible by an assay based upon amplification of a 266 base pair PCR fragment of the human histamine $H_2$ receptor gene, followed by specific acrylamide gel electrophoresis. (it will be apparent to those skilled in the art that single base changes may also be detected by other techniques known to those in the art, including, chemical cleavage, PCR thermoligase reactions, restriction endonuclease digestion of human histamine $H_2$ receptor gene PCR fragments etc.)

Samples of blood are collected from human volunteers into EDTA coated tubes. 1 ml of this blood is heated to 100° C. for 15 minutes and then spun in a microcentrifuge at 13,000 Xg for 15 minutes. The supernatant is collected and the cell debris is discarded. 1 μl of the supernatant is utilised as template DNA for a PCR reaction to amplify a portion of the human histamine $H_2$ receptor gene between bases 501 and 766. The conditions for this PCR reaction are 3 mM $MgCl_2$(Gibco BRL), 1XPCR buffer (Gibco BRL), 0.2 mM of each dATP, dCTP, dTTP, dGTP (Gibco BRL) 10 pmoles of each of oligonucleotide primers 12) and 13) (hereinbefore described) and 1 unit Taq DNA polymerase, in a total volume adjusted to 50 μl by sterile DNAse free water. This mix is then subjected to the following conditions in a Progene thermal cycler (Techne); 96° C., 5 minutes, then 35 cycles of 96° C., 45 seconds, 56° C., 45 seconds, 72° C., 45 seconds.

10 μl of the resultant product is analysed on a 1% agarose gel to ensure that the above reaction is correctly amplifying the target DNA fragement. Then 7.5 μl of the PCR mix is added to 7.5 μl of 95% formamide, 10 mM EDTA pH 8.0, heated to 10020 C. for 5–10 minute, and then quenched immediately in slushy ice for 5 minutes. 3 μl of 6xblue/orange loading dye is then added (Promega) and the mix is loaded into a 1 mm thick 14% 59:1 (acrylamide:bis-acrylamide) electrophoresis gel containing 2% glycerol, prepared in 0.5xTBE buffer. The gel is run for 18–24 hours at a constant voltage of 260V, at room temperature. The gel is then fixed in 10% methanol, 10% ethanoic acid for 10 minutes. The gel is next placed into 1 mg/ml silver nitrate for 15 minutes, then rinsed briefly with distilled water. The gel is then placed into 0.26% formaldehyde, 0.38 M sodium hydroxide for 15 minutes. The gel is finally placed into 0.75% sodium carbonate for 10 minutes.

Figure 1:
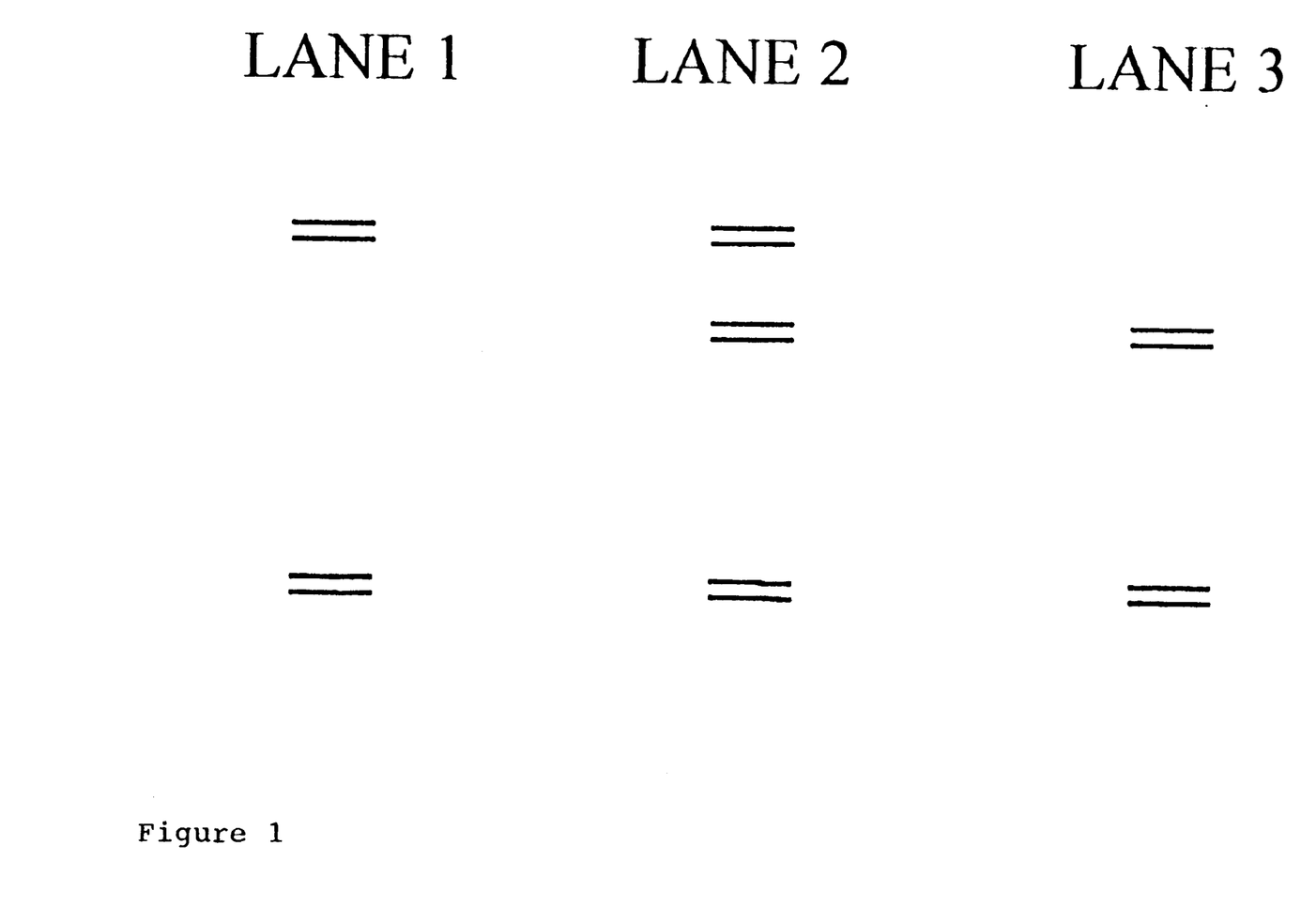

Typical results are illustrated diagrammatically in FIG. 1 which shows a SSCP gel, prepared as above described, on which different samples have been loaded. The following patterns of banding are seen:

Lane 1 shows a pattern corresponding to a homozygons $H_2R_{649G}$ genotype.

Lane 2 shows patterns corresponding to an individual heterozygons $H_2R_{649A}/H_2R_{649G}$ genotype.

Lane 3 shows a pattern corresponding to a homozygous $H_2R_{649A}$ genotype.

Alternative embodiments of the invention can be envisaged by those skilled in the art from the Information contained herein. All such alternative embodiments are Intended to lie within the scope of this application.

The reader's attention is directed to all papers and documents which are filed concurrently with this specification and which are open to public inspection with this specification, and the contents of all such papers and documents are incorporated herein by reference.

All the features disclosed in this specification (including any accompanying claims, abstract and drawings), and/or all of the steps or any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiments. This invention extends to any novel one, or any novel combination, of the features disclosed in this specification (including any accompanying claims, abstract and drawings), or to any novel one, or any novel combination, of the steps of any method or process so disclosed.

What is claimed is:

1. An isolated nucleic acid consisting essentially of a nucleotide sequence selected from the group consisting of SEQ ID NO:12, SEQ ID NO:13, SEQ ID NO:14, and SEQ ID NO:15.

2. A method of amplifying a nucleic acid, the method comprising
   hybridizing the isolated nucleic acid of claim 1 to a target nucleic acid,
   extending the 3' end of the isolated nucleic acid and amplifying the extension product using a polymerase, whereby the target nucleic acid is a template for the extending.

3. The method of claim 2, further comprising denaturing the extended isolated nucleic acid and repeating the hybridizing and extending steps.

4. A method of sequencing a nucleic acid, the method comprising
   hybridizing the isolated nucleic acid of claim 1 to a target nucleic acid,
   extending the 3' end of the isolated nucleic acid using a polymerase, in the presence of dideoxy nucleotides whereby the target nucleic acid is a template for the extending and determining the nucleotide sequence of the extension product.

5. A method of detecting the presence of a nucleic acid encoding a human H2 receptor, the method comprising
   performing the method of claim 2 to form an amplified product,
   isolating nucleic acids in the amplified product on a gel by electrophoresis, and
   determining the presence of a band at a pre-determined position on the gel, wherein the presence of the band at the pre-determined position indicates the presence of the nucleic acid encoding the human H2 receptor.

6. A kit comprising the nucleic acid of claim 1.

7. The kit of claim 6, further comprising a restriction endonuclease.

8. A method of detecting a polymorphism in a nucleic acid encoding a human H2 receptor, the method comprising hybridizing the nucleic acid of claim 1 to a target nucleic acid to form an at least partially doublestranded hybrid nucleic acid, isolating the hybrid nucleic acid on a gel by electrophoresis, and determining the presence of a band at a pre-determined position on a gel, wherein the presence of the band at the pre-determined position indicates the presence of the polymorphism.

9. The method of claim 8, further comprising amplifying the target nucleic acid before the hybridizing step.

10. A method of detecting a polymorphism in a nucleic acid encoding a human H2 receptor, the method comprising determining, by single-stranded conformational polymorphism analysis, whether the nucleic acid comprises SEQ ID NO:18 with at least one nucleotide substitution selected from the group consisting of T to C at position 398, A to T at position 525, A to G at position 620, A to G at position 649, A to G at position 692, and G to A at position 802, each nucleotide position being relative to SEQ ID NO:18.

* * * * *

SEQUENCE LISTING

<160> NUMBER OF SEQ ID NOS: 19

<210> SEQ ID NO 1
<211> LENGTH: 413
<212> TYPE: DNA

```
<213> ORGANISM: Homo sapiens

<220> FEATURE:
<221> NAME/KEY: CDS
<222> LOCATION: (3)...(410)

<400> SEQUENCE: 1 ca gct cgg gtc gcc atc tct ctg gtc tta att tgg gtc atc tcc att        47
   Ala Arg Val Ala Ile Ser Leu Val Leu Ile Trp Val Ile Ser Ile
    1               5                  10                  15 acc ctg tcc ttt ctg tct atc cac ctg ggg tgg aac agc agg aac gag       95
Thr Leu Ser Phe Leu Ser Ile His Leu Gly Trp Asn Ser Arg Asn Glu
                 20                  25                  30 agc agc aag ggc aat cat acc acc tct aag tgc aat gtc cag gtc aat      143
Thr Ser Lys Gly Asn His Thr Thr Ser Lys Cys Asn Val Gln Val Asn
             35                  40                  45 gaa gtg tac ggg ctg gtg gat ggg ctg gtc acc ttc tac ctc ccg cta      191
Glu Val Tyr Gly Leu Val Asp Gly Leu Val Thr Phe Tyr Leu Pro Leu
         50                  55                  60 ctg atc atg tgc atc acc tac tac cgc atc ttc agg gtc gcc cgg gat      239
Leu Ile Met Cys Ile Thr Tyr Tyr Arg Ile Phe Arg Val Ala Arg Asp
     65                  70                  75 cag gcc aag agg atc gat cac att agc tcc tgg aag gca gcc acc atc      287
Gln Ala Lys Arg Ile Asp His Ile Ser Ser Trp Lys Ala Ala Thr Ile
 80                  85                  90                  95 agg gag cac aga gcc aca gtg aca ctg gcc gcc gtc atg ggg gcc ttc      335
Arg Glu His Arg Ala Thr Val Thr Leu Ala Ala Val Met Gly Ala Phe
                100                 105                 110 atc atc tgc tgg ttt ccc tac ttc acc gcg ttt gtg tac cgt ggg ctg      383
Ile Ile Cys Trp Phe Pro Tyr Phe Thr Ala Phe Val Tyr Arg Gly Leu
            115                 120                 125 aga ggg gat gat gcc atc aat gag atg tta                              413
Arg Gly Asp Asp Ala Ile Asn Glu Met
        130                 135

<210> SEQ ID NO 2
<211> LENGTH: 1046
<212> TYPE: DNA
<213> ORGANISM: Homo sapiens

<220> FEATURE:
<221> NAME/KEY: CDS
<222> LOCATION: (3)...(1046)

<400> SEQUENCE: 2 cc aat ggc aca gcc tct tcc ttt tgc ctg gac tct acc gca tgc aag        47
   Asn Gly Thr Ala Ser Ser Phe Cys Leu Asp Ser Thr Ala Cys Lys
    1               5                  10                  15 atc acc atc acc gtg gtc ctt gcg gtc ctc atc ctc atc acc gtt gct       95
Ile Thr Ile Thr Val Val Leu Ala Val Leu Ile Leu Ile Thr Val Ala
                 20                  25                  30 ggc aat gtg gtc gtc tgt ctg gcc gtg ggc ttg aac cgc cgg ctc cgc      143
Gly Asn Val Val Val Cys Leu Ala Val Gly Leu Asn Arg Arg Leu Arg
             35                  40                  45 aac ctg acc aat tgt ttc atc gtg tcc ttg gct atc act gac ctg ctc      191
Asn Leu Thr Asn Cys Phe Ile Val Ser Leu Ala Ile Thr Asp Leu Leu
         50                  55                  60 ctc ggc ctc ctg gtg ctg ccc ttc tct gcc atc tac cag ctg tcc tgc      239
Leu Gly Leu Leu Val Leu Pro Phe Ser Ala Ile Tyr Gln Leu Ser Cys
     65                  70                  75 aag tgg agc ttt ggc aag gtc ttc tgc aat atc tac acc agc ctg gat      287
Lys Trp Ser Phe Gly Lys Val Phe Cys Asn Ile Tyr Thr Ser Leu Asp
 80                  85                  90                  95
```

```
gtg atg ctc tgc aca gcc tcc att ctt aac ctc ttc atg atc agc ctc      335
Val Met Leu Cys Thr Ala Ser Ile Leu Asn Leu Phe Met Ile Ser Leu
            100                 105                 110 gac cgg tac tgc gct gtc atg gac cca ctg cgg tac cct gtg ctg gtc      383
Asp Arg Tyr Cys Ala Val Met Asp Pro Leu Arg Tyr Pro Val Leu Val
            115                 120                 125 acc cca gct cgg gtc gcc atc tct ctg gtc tta att tgg gtc atc tcc      431
Thr Pro Ala Arg Val Ala Ile Ser Leu Val Leu Ile Trp Val Ile Ser
            130                 135                 140 att acc ctg tcc ttt ctg tct atc cac ctg ggg tgg aac agc agg aac      479
Ile Thr Leu Ser Phe Leu Ser Ile His Leu Gly Trp Asn Ser Arg Asn
        145                 150                 155 gag acc agc aag ggc aat cat acc acc tct aag tgc aat gtc cag gtc      527
Glu Thr Ser Lys Gly Asn His Thr Thr Ser Lys Cys Asn Val Gln Val
160                 165                 170                 175 aat gaa gtg tac ggg ctg gtg gat ggg ctg gtc acc ttc tac ctc ccg      575
Asn Glu Val Tyr Gly Leu Val Asp Gly Leu Val Thr Phe Tyr Leu Pro
                180                 185                 190 cta ctg atc atg tgc atc acc tac tac cgc atc ttc agg gtc gcc cgg      623
Leu Leu Ile Met Cys Ile Thr Tyr Tyr Arg Ile Phe Arg Val Ala Arg
            195                 200                 205 gat cag gcc aag agg atc gat cac att agc tcc tgg aag gca gcc acc      671
Asp Gln Ala Lys Arg Ile Asp His Ile Ser Ser Trp Lys Ala Ala Thr
210                 215                 220 atc agg gag cac aga gcc aca gtg aca ctg gcc gcc gtc atg ggg gcc      719
Ile Arg Glu His Arg Ala Thr Val Thr Leu Ala Ala Val Met Gly Ala
        225                 230                 235 ttc atc atc tgc tgg ttt ccc tac ttc acc gcg ttt gtg tac cgt ggg      767
Phe Ile Ile Cys Trp Phe Pro Tyr Phe Thr Ala Phe Val Tyr Arg Gly
240                 245                 250                 255 ctg aga ggg gat gat gcc atc aat gag atg tta gaa gcc atc gtt ctg      815
Leu Arg Gly Asp Asp Ala Ile Asn Glu Met Leu Glu Ala Ile Val Leu
                260                 265                 270 tgg ctg ggc tat gcc aac tca gcc ctg aac ccc atc ctg tat gct gcg      863
Trp Leu Gly Tyr Ala Asn Ser Ala Leu Asn Pro Ile Leu Tyr Ala Ala
            275                 280                 285 ctg aac aga gac ttc cgc acc ggg tac caa cag ctc ttc tgc tgc agg      911
Leu Asn Arg Asp Phe Arg Thr Gly Tyr Gln Gln Leu Phe Cys Cys Arg
        290                 295                 300 ctg gcc aac cgc aac tcc cac aaa act tct ctg agg tcc aac gcc tct      959
Leu Ala Asn Arg Asn Ser His Lys Thr Ser Leu Arg Ser Asn Ala Ser
305                 310                 315 cag ctg tcc agg acc caa agc cga gaa ccc agg caa cag gaa gag aaa     1007
Gln Leu Ser Arg Thr Gln Ser Arg Glu Pro Arg Gln Gln Glu Glu Lys
                320                 325                 330                 335 ccc ctg aag ctc cag gtg tgg agt ggg aca gaa gtc acg                 1046
Pro Leu Lys Leu Gln Val Trp Ser Gly Thr Glu Val Thr
            340                 345
```

<210> SEQ ID NO 3
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 3
ccaatggcac agcctctt                                                     18

```
<210> SEQ ID NO 4
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 4
cgtgacttct gtcccact                                                 18

<210> SEQ ID NO 5
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 5
ccaggcaaca ggaagaga                                                 18

<210> SEQ ID NO 6
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 6
tctcttcctg ttgcctgg                                                 18

<210> SEQ ID NO 7
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 7
gcagcagaag agctgttg                                                 18

<210> SEQ ID NO 8
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 8
tccaggtcaa tgaagtgt                                                 18

<210> SEQ ID NO 9
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 9
acacttcatt gacctgga                                                 18

<210> SEQ ID NO 10
```

```
<211> LENGTH: 18
<212> TYPE: DNA
<213> ORGANISM: Artificial Sequence

<220> FEATURE:
<223> OTHER INFORMATION: Synthetically generated oligonucleotide

<400> SEQUENCE: 10
ccaagaggat caatcaca                                                    18

<210> SEQ ID NO 11
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 11
tgtgattgat cctcttgg                                                    18

<210> SEQ ID NO 12
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 12
acaccagcct ggatgtga                                                    18

<210> SEQ ID NO 13
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 13
tcacatccag gctggtgt                                                    18

<210> SEQ ID NO 14
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 14
caatcatacc acctctaa                                                    18

<210> SEQ ID NO 15
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 15
acacaaacgc ggtgaagt                                                    18

<210> SEQ ID NO 16
<211> LENGTH: 136
```

```
<212> TYPE: PRT
<213> ORGANISM: Homo sapiens

<400> SEQUENCE: 16

Ala Arg Val Ala Ile Ser Leu Val Leu Ile Trp Val Ile Ser Ile Thr
 1               5                  10                  15

Leu Ser Phe Leu Ser Ile His Leu Gly Trp Asn Ser Arg Asn Glu Thr
            20                  25                  30

Ser Lys Gly Asn His Thr Thr Ser Lys Cys Asn Val Gln Val Asn Glu
        35                  40                  45

Val Tyr Gly Leu Val Asp Gly Leu Val Thr Phe Tyr Leu Pro Leu Leu
    50                  55                  60

Ile Met Cys Ile Thr Tyr Tyr Arg Ile Phe Arg Val Ala Arg Asp Gln
65                  70                  75                  80

Ala Lys Arg Ile Asp His Ile Ser Ser Trp Lys Ala Ala Thr Ile Arg
                85                  90                  95

Glu His Arg Ala Thr Val Thr Leu Ala Ala Val Met Gly Ala Phe Ile
            100                 105                 110

Ile Cys Trp Phe Pro Tyr Phe Thr Ala Phe Val Tyr Arg Gly Leu Arg
        115                 120                 125

Gly Asp Asp Ala Ile Asn Glu Met
    130                 135

<210> SEQ ID NO 17
<211> LENGTH: 348
<212> TYPE: PRT
<213> ORGANISM: Homo sapiens

<400> SEQUENCE: 17

Asn Gly Thr Ala Ser Ser Phe Cys Leu Asp Ser Thr Ala Cys Lys Ile
 1               5                  10                  15

Thr Ile Thr Val Val Leu Ala Val Leu Ile Leu Ile Thr Val Ala Gly
            20                  25                  30

Asn Val Val Val Cys Leu Ala Val Gly Leu Asn Arg Arg Leu Arg Asn
        35                  40                  45

Leu Thr Asn Cys Phe Ile Val Ser Leu Ala Ile Thr Asp Leu Leu Leu
    50                  55                  60

Gly Leu Leu Val Leu Pro Phe Ser Ala Ile Tyr Gln Leu Ser Cys Lys
65                  70                  75                  80

Trp Ser Phe Gly Lys Val Phe Cys Asn Ile Tyr Thr Ser Leu Asp Val
                85                  90                  95

Met Leu Cys Thr Ala Ser Ile Leu Asn Leu Phe Met Ile Ser Leu Asp
            100                 105                 110

Arg Tyr Cys Ala Val Met Asp Pro Leu Arg Tyr Pro Val Leu Val Thr
        115                 120                 125

Pro Ala Arg Val Ala Ile Ser Leu Val Leu Ile Trp Val Ile Ser Ile
    130                 135                 140

Thr Leu Ser Phe Leu Ser Ile His Leu Gly Trp Asn Ser Arg Asn Glu
145                 150                 155                 160

Thr Ser Lys Gly Asn His Thr Thr Ser Lys Cys Asn Val Gln Val Asn
                165                 170                 175

Glu Val Tyr Gly Leu Val Asp Gly Leu Val Thr Phe Tyr Leu Pro Leu
            180                 185                 190

Leu Ile Met Cys Ile Thr Tyr Tyr Arg Ile Phe Arg Val Ala Arg Asp
        195                 200                 205
```

-continued

```
Gln Ala Lys Arg Ile Asp His Ile Ser Ser Trp Lys Ala Ala Thr Ile
        210                 215                 220

Arg Glu His Arg Ala Thr Val Thr Leu Ala Ala Val Met Gly Ala Phe
225                 230                 235                 240

Ile Ile Cys Trp Phe Pro Tyr Phe Thr Ala Phe Val Tyr Arg Gly Leu
                245                 250                 255

Arg Gly Asp Asp Ala Ile Asn Glu Met Leu Glu Ala Ile Val Leu Trp
            260                 265                 270

Leu Gly Tyr Ala Asn Ser Ala Leu Asn Pro Ile Leu Tyr Ala Ala Leu
        275                 280                 285

Asn Arg Asp Phe Arg Thr Gly Tyr Gln Gln Leu Phe Cys Cys Arg Leu
290                 295                 300

Ala Asn Arg Asn Ser His Lys Thr Ser Leu Arg Ser Asn Ala Ser Gln
305                 310                 315                 320

Leu Ser Arg Thr Gln Ser Arg Glu Pro Arg Gln Gln Glu Glu Lys Pro
                325                 330                 335

Leu Lys Leu Gln Val Trp Ser Gly Thr Glu Val Thr
                340                 345
```

<210> SEQ ID NO 18
<211> LENGTH: 1191
<212> TYPE: DNA
<213> ORGANISM: Homo sapiens

<220> FEATURE:
<221> NAME/KEY: CDS
<222> LOCATION: (1)...(1077)

<400> SEQUENCE: 18

```
atg gca ccc aat ggc aca gcc tct tcc ttt tgc ctg gac tct acc gca        48
Met Ala Pro Asn Gly Thr Ala Ser Ser Phe Cys Leu Asp Ser Thr Ala
 1               5                  10                  15 tgc aag atc acc atc acc gtg gtc ctt gcg gtc ctc atc ctc atc acc        96
Cys Lys Ile Thr Ile Thr Val Val Leu Ala Val Leu Ile Leu Ile Thr
             20                  25                  30 gtt gct ggc aat gtg gtc gtc tgt ctg gcc gtg ggc ttg aac cgc cgg       144
Val Ala Gly Asn Val Val Val Cys Leu Ala Val Gly Leu Asn Arg Arg
         35                  40                  45 ctc cgc aac ctg acc aat tgt ttc atc gtg tcc ttg gct atc act gac       192
Leu Arg Asn Leu Thr Asn Cys Phe Ile Val Ser Leu Ala Ile Thr Asp
     50                  55                  60 ctg ctc ctc ggc ctc ctg gtg ctg ccc ttc tct gcc atc tac cag ctg       240
Leu Leu Leu Gly Leu Leu Val Leu Pro Phe Ser Ala Ile Tyr Gln Leu
 65                  70                  75                  80 tcc tgc aag tgg agc ttt ggc aag gtc ttc tgc aat atc tac acc agc       288
Ser Cys Lys Trp Ser Phe Gly Lys Val Phe Cys Asn Ile Tyr Thr Ser
                 85                  90                  95 ctg gat gtg atg ctc tgc aca gcc tcc att ctt aac ctc ttc atg atc       336
Leu Asp Val Met Leu Cys Thr Ala Ser Ile Leu Asn Leu Phe Met Ile
            100                 105                 110 agc ctc gac cgg tac tgc gct gtc atg gac cca ctg cgg tac cct gtg       384
Ser Leu Asp Arg Tyr Cys Ala Val Met Asp Pro Leu Arg Tyr Pro Val
        115                 120                 125 ctg gtc acc cca gtt cgg gtc gcc atc tct ctg gtc tta att tgg gtc       432
Leu Val Thr Pro Val Arg Val Ala Ile Ser Leu Val Leu Ile Trp Val
    130                 135                 140 atc tcc att acc ctg tcc ttt ctg tct atc cac ctg ggg tgg aac agc       480
Ile Ser Ile Thr Leu Ser Phe Leu Ser Ile His Leu Gly Trp Asn Ser
145                 150                 155                 160
```

```
agg aac gag acc agc aag ggc aat cat acc acc tct aag tgc aaa gtc       528
Arg Asn Glu Thr Ser Lys Gly Asn His Thr Thr Ser Lys Cys Lys Val
                165                 170                 175 cag gtc aat gaa gtg tac ggg ctg gtg gat ggg ctg gtc acc ttc tac       576
Gln Val Asn Glu Val Tyr Gly Leu Val Asp Gly Leu Val Thr Phe Tyr
            180                 185                 190 ctc ccg cta ctg atc atg tgc atc acc tac tac cgc atc ttc aag gtc       624
Leu Pro Leu Leu Ile Met Cys Ile Thr Tyr Tyr Arg Ile Phe Lys Val
        195                 200                 205 gcc cgg gat cag gcc aag agg atc aat cac att agc tcc tgg aag gca       672
Ala Arg Asp Gln Ala Lys Arg Ile Asn His Ile Ser Ser Trp Lys Ala
    210                 215                 220 gcc acc atc agg gag cac aaa gcc aca gtg aca ctg gcc gcc gtc atg       720
Ala Thr Ile Arg Glu His Lys Ala Thr Val Thr Leu Ala Ala Val Met
225                 230                 235                 240 ggg gcc ttc atc atc tgc tgg ttt ccc tac ttc acc gcg ttt gtg tac       768
Gly Ala Phe Ile Ile Cys Trp Phe Pro Tyr Phe Thr Ala Phe Val Tyr
                245                 250                 255 cgt ggg ctg aga ggg gat gat gcc atc aat gag gtg tta gaa gcc atc       816
Arg Gly Leu Arg Gly Asp Asp Ala Ile Asn Glu Val Leu Glu Ala Ile
            260                 265                 270 gtt ctg tgg ctg ggc tat gcc aac tca gcc ctg aac ccc atc ctg tat       864
Val Leu Trp Leu Gly Tyr Ala Asn Ser Ala Leu Asn Pro Ile Leu Tyr
        275                 280                 285 gct gcg ctg aac aga gac ttc cgc acc ggg tac caa cag ctc ttc tgc       912
Ala Ala Leu Asn Arg Asp Phe Arg Thr Gly Tyr Gln Gln Leu Phe Cys
    290                 295                 300 tgc agg ctg gcc aac cgc aac tcc cac aaa act tct ctg agg tcc aac       960
Cys Arg Leu Ala Asn Arg Asn Ser His Lys Thr Ser Leu Arg Ser Asn
305                 310                 315                 320 gcc tct cag ctg tcc agg acc caa agc cga gaa ccc agg caa cag gaa      1008
Ala Ser Gln Leu Ser Arg Thr Gln Ser Arg Glu Pro Arg Gln Gln Glu
                325                 330                 335 gag aaa ccc ctg aag ctc cag gtg tgg agt ggg aca gaa gtc acg gcc      1056
Glu Lys Pro Leu Lys Leu Gln Val Trp Ser Gly Thr Glu Val Thr Ala
            340                 345                 350 ccc cag gga gcc aca gac agg taaaagctcc aggtgtggag tgggacagaa         1107
Pro Gln Gly Ala Thr Asp Arg
        355 gtcacggccc cccagggagc cacagacagg taagcgctga acagagactt ccgcaccggg    1167 taccaacagc tcttctgctg cagg                                           1191

<210> SEQ ID NO 19
<211> LENGTH: 359
<212> TYPE: PRT
<213> ORGANISM: Homo sapiens

<400> SEQUENCE: 19

Met Ala Pro Asn Gly Thr Ala Ser Ser Phe Cys Leu Asp Ser Thr Ala
 1               5                  10                  15

Cys Lys Ile Thr Ile Thr Val Val Leu Ala Val Leu Ile Leu Ile Thr
            20                  25                  30

Val Ala Gly Asn Val Val Cys Leu Ala Val Gly Leu Asn Arg Arg
        35                  40                  45

Leu Arg Asn Leu Thr Asn Cys Phe Ile Val Ser Leu Ala Ile Thr Asp
    50                  55                  60

Leu Leu Leu Gly Leu Leu Val Leu Pro Phe Ser Ala Ile Tyr Gln Leu
65                  70                  75                  80
```

```
Ser Cys Lys Trp Ser Phe Gly Lys Val Phe Cys Asn Ile Tyr Thr Ser
             85              90                  95

Leu Asp Val Met Leu Cys Thr Ala Ser Ile Leu Asn Leu Phe Met Ile
            100             105             110

Ser Leu Asp Arg Tyr Cys Ala Val Met Asp Pro Leu Arg Tyr Pro Val
        115             120             125

Leu Val Thr Pro Val Arg Val Ala Ile Ser Leu Val Leu Ile Trp Val
        130             135             140

Ile Ser Ile Thr Leu Ser Phe Leu Ser Ile His Leu Gly Trp Asn Ser
145             150             155                     160

Arg Asn Glu Thr Ser Lys Gly Asn His Thr Thr Ser Lys Cys Lys Val
                165             170             175

Gln Val Asn Glu Val Tyr Gly Leu Val Asp Gly Leu Val Thr Phe Tyr
            180             185             190

Leu Pro Leu Leu Ile Met Cys Ile Thr Tyr Tyr Arg Ile Phe Lys Val
        195             200             205

Ala Arg Asp Gln Ala Lys Arg Ile Asn His Ile Ser Ser Trp Lys Ala
        210             215             220

Ala Thr Ile Arg Glu His Lys Ala Thr Val Thr Leu Ala Ala Val Met
225             230             235             240

Gly Ala Phe Ile Ile Cys Trp Phe Pro Tyr Phe Thr Ala Phe Val Tyr
                245             250             255

Arg Gly Leu Arg Gly Asp Asp Ala Ile Asn Glu Val Leu Glu Ala Ile
            260             265             270

Val Leu Trp Leu Gly Tyr Ala Asn Ser Ala Leu Asn Pro Ile Leu Tyr
        275             280             285

Ala Ala Leu Asn Arg Asp Phe Arg Thr Gly Tyr Gln Gln Leu Phe Cys
        290             295             300

Cys Arg Leu Ala Asn Arg Asn Ser His Lys Thr Ser Leu Arg Ser Asn
305             310             315             320

Ala Ser Gln Leu Ser Arg Thr Gln Ser Arg Glu Pro Arg Gln Gln Glu
                325             330             335

Glu Lys Pro Leu Lys Leu Gln Val Trp Ser Gly Thr Glu Val Thr Ala
            340             345             350

Pro Gln Gly Ala Thr Asp Arg
            355
```